United States Patent
Ancell

(10) Patent No.: US 7,112,712 B1
(45) Date of Patent: Sep. 26, 2006

(54) DRESSING

(75) Inventor: William Ancell, Winchester (GB)

(73) Assignee: Protex Healthcare (UK) Limited, Wokingham (GB)

( * ) Notice: Subject to any disclaimer, the term of this patent is extended or adjusted under 35 U.S.C. 154(b) by 129 days.

(21) Appl. No.: 10/129,624

(22) PCT Filed: Nov. 10, 1999

(86) PCT No.: PCT/GB00/04300

§ 371 (c)(1),
(2), (4) Date: Oct. 8, 2002

(87) PCT Pub. No.: WO01/34079

PCT Pub. Date: May 17, 2001

(30) Foreign Application Priority Data

Nov. 10, 1999 (GB) .................. 9926632.2

(51) Int. Cl.
*A61F 13/00* (2006.01)
*A61F 15/00* (2006.01)

(52) U.S. Cl. .................... 602/41; 602/43; 602/44; 602/56; 602/58

(58) Field of Classification Search .......... 602/41–59, 602/304–308; 128/888, 889
See application file for complete search history.

(56) References Cited

U.S. PATENT DOCUMENTS

| | | | |
|---|---|---|---|
| 3,703,897 A | 11/1972 | Mack et al. | |
| 4,211,227 A | 7/1980 | Anderson et al. | |
| 4,219,019 A | 8/1980 | Coates | |
| 4,622,089 A | 11/1986 | Lauritzen | |
| 4,832,852 A * | 5/1989 | Wells et al. | 210/671 |
| 6,103,951 A | 8/2000 | Freeman | |

FOREIGN PATENT DOCUMENTS

| | | |
|---|---|---|
| EP | 0 070 164 A | 1/1983 |
| EP | 0 151 018 | 8/1985 |
| EP | 0 171 807 A | 2/1986 |
| GB | 960 427 | 6/1964 |
| GB | 1 110 016 | 4/1968 |
| GB | 1 130 857 A | 10/1968 |
| GB | 1 242 717 A | 8/1971 |
| GB | 1 453 701 | 10/1976 |
| GB | 2 024 709 | 1/1980 |
| GB | 2 055 581 A | 3/1981 |
| GB | 2 302 669 | 1/1997 |
| GB | 2 356 145 | 5/2001 |
| WO | 84 03833 A | 10/1984 |
| WO | WO 00/18343 | 4/2000 |

OTHER PUBLICATIONS

T. Ross, "A Primer in Digital Textile Printing" May 2001 (http://www.techexchange.com/thelibrary/DTP101.html).

(Continued)

*Primary Examiner*—Henry Bennett
*Assistant Examiner*—Amanda Wieker
(74) *Attorney, Agent, or Firm*—Nixon & Vanderhye P.C.

(57) ABSTRACT

A dressing and a method of manufacturing a dressing. The dressing comprising an absorbent support fabric (2), and a polyester fiber sheet (1) attached to one surface of the absorbent support fabric to provide a wicking path such that exudates contacting an outer surface of the fiber sheet are wicked to the absorbent support fabric. The outer surface of the polyester fiber sheet is heat treated to hinder individual fibers from extending out of the surface and thereby produce a glazed effect. This glazed surface inhibits the dressing from sticking to a wound, and impedes exudate transported within the dressing from returning to the dressing surface.

20 Claims, 1 Drawing Sheet

OTHER PUBLICATIONS

Section 3-1: Classification of Wound Management Materials—(United Section), 1996 (http://www.smtl.co.uk/WMPRC/VFM-report/VFM-Chapter3-1.html).

H. Griesser, "P84-Polymide Fibres in Nonwoven Applications" (http://members.eunet.at/h.griesser/shanghai/Shanghai.htm).

AM Medical Fabrics Limited, 1996, p. 11.

L. Russell et al., "Drawtex: a unique dressing that can be tailor-made to fit wounds" *British Journal of Nursing*, vol. 8, No. 15, 1999, pp. 1022-1026.

* cited by examiner

DRESSING

This application is the US national phase of international application PCT/GB00/04300 filed 9 Nov. 2000, which designated the US.

BACKGROUND OF THE INVENTION

1. Field of the Invention

This invention relates to a dressing for transporting exudates and other fluids away from a wound and a method of manufacturing such a dressing.

2. Discussion of Prior Art

In the field of wound dressings, for example, with absorbent wound dressings or surgical drains, different types of absorbent fabrics are used to absorb exudates emanating from a wound bed. One of the problems with many absorbent fabrics is that they tend to stick to the wound. This can cause the healing wound to be disturbed on removal of the dressing and furthermore, surface fibres from the dressing may come off and be left in the wound. Another problem is that the absorbed exudate is transported along the fabric and may come into contact with other non-infected parts of the wound that the dressing covers; this can cause infection of these areas.

There is therefore a desire in the field of wound dressings to provide a dressing with a high absorbency and a high rate of transportation of exudate away from a wound bed, while reducing any risk of reinfection of the wound caused by the spreading of exudate across non-infected areas of the wound. There is also a desire to provide a dressing that does not "stick" to the wound, whilst insulating and maintaining a moist environment for the wound.

One known way of addressing the above problems is to use perforated plastic films and laminates between the wound dressing and the wound bed. These films help reduce the adhesion of the dressing and the danger of exudates that are transported within the dressing contacting non-infected parts of the wound bed. These films, have the disadvantage, however, of hindering the absorbency rate of the exudate, as the perforations in the film are not sufficient to maximise absorbency. This may cause the exudate to remain on the wound site for longer. Another drawback with plastic films is that they are often less flexible and not as soft as the absorbent fabric. This can lead to the dressing being uncomfortable or painful when applied to a wound. It can also lead to problems for nursing staff when they try to cut the fabric for the wounds into complicated shapes to cover, for example, mobile joints. The plastic films are also fragile and easily damaged. This can lead to the absorbent fabric contacting the wound directly in certain places, with the risk of reinfection and sticking that this entails.

GB-A-1130857 discloses a dressing comprising a plurality of layers needle punched together. The outer wound contacting layer comprises a batt of polypropylene fibres produced by a carding machine, this is needled to an absorptive cellulose layer or cotton wadding layer which in turn is attached to a rayon layer. The surface of the polypropylene layer is heat treated.

U.S. Pat. No. 4,211,227 discloses a nonwoven surgical sponge material having an inner core of rayon and polyester mix and a pair of outer layers of polyester fibres. The material is bonded by passing it through heated rollers.

GB-A-2302669 discloses a dressing having two outer fibre batts needle punched to an inner screen formed of 80% polyester and 20% cotton yarns.

SUMMARY OF THE INVENTION

In accordance with the present invention there is provided a dressing for transporting exudates and other fluids away from a wound, the dressing comprising a plurality of synthetic fibres and an absorbent fabric; wherein at least a part of an outer surface of the dressing constituted by a surface of the plurality of directional synthetic fibres, is heat treated to hinder individual fibres from extending out of that part of the surface, giving a glazed effect to that part of the outer surface; characterised in that:

the plurality of synthetic fibres comprise directional fibres arranged to provide a wicking path along the directional fibres from the outer surface of the dressing to a surface of the absorbent fabric, such that fluids contacting the outer surface are wicked away from the outer surface along the synthetic fibres towards the absorbent fabric.

The heat treatment of the synthetic fibres produces a smooth porous surface that facilitates the non-adhesion of the dressing to a wound face. This is due to the glazed surface, which repels cellular attachment during granulation without significantly reducing absorbency of exudate or other fluids. This means that a wound dressing can be changed without compromising the healing of the wound by removing initial granulation. Furthermore, the heat treatment anchors the fibres to the dressing reducing the risk of them becoming detached from the dressing and remaining in the wound when the dressing is removed. Additionally, the glazed finish impedes exudates that are transported within the dressing beneath the glazed surface from returning to the wound face in any significant quantities. The absorbency of the dressing also acts to encourage blood flow to the region and thereby promotes healing.

Although the dressing could be made from many different types of synthetic fibres, in preferred embodiments the synthetic fibres are polyester fibres. Polyester fibres are particularly well adapted, being cheap, easy to manipulate and having good wicking properties.

In some embodiments, the absorbent fabric comprises a woven fabric. Woven fabrics are well adapted for mounting synthetic fibres.

In preferred embodiments the absorbent fabric comprises a mixed yarn of between 60% and 70% polyester and 40% and 30% cotton, most preferably substantially 65% polyester and 35% cotton. It has been found that this composition of fabric has surprisingly good absorption properties, being able to absorb up to thirty four times its weight in fluids. Furthermore, this proportion of cotton traps odours particularly well, while the polyester content acts to wick fluid to the outside edge of the dressing.

Although the fabric may be woven from a variety of different sized threads, threads with an average diameter of 68 nm have been found to be particularly appropriate.

Although in some embodiments only a portion of the outer surface is heat treated, in preferred embodiments the whole of the first outer surface is heat-treated.

Preferably, the outer surface is a first outer surface, and the dressing further comprises a plurality of synthetic fibres arranged to provide a wicking path from a second outer surface of the dressing to a further surface of the absorbent fabric, wherein the second outer surface faces away from the first outer surface. This produces a wicking path on the other side of the absorbent fabric to the first wicking path, enabling fluid to pass from the absorbent material along this path to further absorbent materials which may be placed in contact with the second wicking path.

In some embodiments the second outer surface is heat treated to hinder the synthetic fibres from extending out of the surface, giving a glazed effect to the second outer surface. Heat treatment of the second outer surface enables sticky tape to be easily removed from this surface without unduly disturbing the dressing.

A preferred density for the substantially planar dressing, giving particularly good absorbency and transport properties, is between 710 and 735 g/m$^2$.

In preferred embodiments, the dressing comprises two dressings arranged adjacent to each other such that respective outer surfaces of the two dressings contact each other. This arrangement allows the amount of fluid that the dressing can absorb to be increased.

Advantageously, it is the second outer surfaces of the dressings that contact each other. The two dressings contacting each other via the synthetic fibres that are not heat-treated, results in the fluids passing particularly easily between the two dressings.

Advantageously, the thickness of the dressing is between 1 and 4 mm, more preferably, between 3 and 3.5 mm. It has been found that this is a particularly advantageous thickness for the dressing, providing a good absorbency without being too unwieldy.

In some embodiments the dressing is arranged to form a drain, preferably, in the form of a strip between 8 and 15 mm wide. The fluid absorption and transporting properties of the dressing make it particularly well adapted as a surgical drain. Furthermore, the fabric structure allows for the original tensile strength to be maintained whilst saturated.

In accordance with a second aspect of the present invention there is provided a dressing for transporting exudates and other fluids away from a wound, the dressing comprising a plurality of synthetic fibres and an absorbent fabric; wherein the plurality of synthetic fibres are arranged to provide a wicking path from an outer surface of the dressing to a surface of the absorbent fabric, such that fluids contacting the outer surface are wicked away from the outer surface along the synthetic fibres towards the absorbent fabric; the absorbent fabric comprising a mixed yarn of between 60% to 70% polyester and 40% to 30% cotton.

It has been found that with the above dressing the synthetic fibres and absorbent dressing have a synergy, acting together to produce excellent absorbent and wicking properties. This composition of absorbent fabric also has a surprisingly good absorbency, holding the absorbed fluid within its structure thereby reducing odours. Furthermore, the absorbent fabric acts in conjunction with the synthetic fibres to wick the fluid away from the wound bed and spread it outwards through the dressing. This helps reduce the wetness of the portion of the dressing contacting the wound bed.

Preferably, the absorbent fabric comprises a mixed yarn of substantially 65% polyester and 35% cotton. This composition of absorbent fabric has surprisingly good absorbency, absorbing up to 34 times its weight in fluid.

In accordance with a third aspect of the present invention there is provided a method of manufacturing a dressing, comprising attaching a plurality of synthetic fibres to one surface of an absorbent central support fabric, such that the synthetic fibres form a wicking path between an outer surface and the absorbent support fabric; and heating at least a part of the outer surface to impede individual fibres from extending out of that part of the surface, thereby giving a glazed effect to that part of the surface.

In preferred embodiments, the surface is heated to a temperature of between 200 and 250° C. It has been found that this temperature range produces an outer surface with a particularly low "stickiness" whilst still having excellent absorption properties.

The surface may be heat treated in a variety of ways, preferably by passing heated rollers over the surface or with a flame that acts to singe the surface.

In preferred embodiments the synthetic fibres are attached to the absorbent support fabric by pushing the synthetic fibres through the support surface using needle punching. This is a convenient and effective way of producing the dressing.

BRIEF DESCRIPTION OF THE DRAWING

Embodiments of the present invention will now be described, by way of example only, and with reference to the accompanying drawing, in which.

DETAILED DISCUSSION OF EMBODIMENTS

Figure 1:
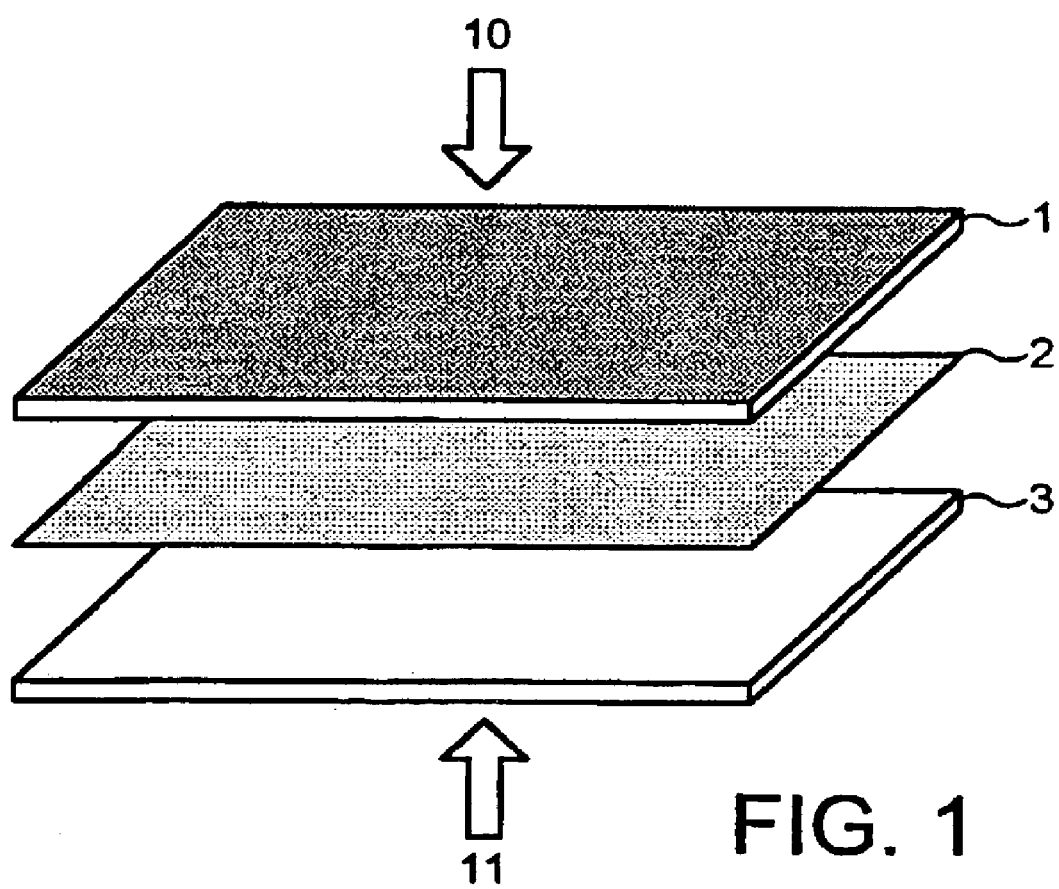
FIG. 1 illustrates a dressing according to an embodiment of the invention.

With reference to FIG. 1, a dressing according to an embodiment of the invention is shown, comprising a polyester fibre sheet 1 of directional fibres of varying filament diameters, the sheet having a thickness of 1.7 mm. The outer surface 10 is heat treated to produce a "glazed" effect, i.e. the fibres at the surface are bound together by the heat producing a smooth surface out of which individual fibres are hindered from extending.

The polyester fibres are attached to a central support polycotton woven fabric sheet 2, which is 0.2 mm thick. They are attached to the central support by conventional needle punching, which produces a felt fabric.

The polycotton support fabric 2 is woven from 65% polyester and 35% cotton threads to give a density of 90 ends and 65 picks after scouring. Apart from the scouring (washing) after weaving, the support fabric will have no additional dying or processing. The scouring process removes residues thereby reducing optical brilliance and contamination in the final dressing and diminishing the risk of any allergic reaction to the dressing. The weight after scouring of the planar dressing is between 120 and 95 g/m$^2$. The cotton content of the support surface holds the fluid in a concentration in the middle of the dressing causing the outer surfaces of the dressing to remain damp rather than wet and reducing any odours emanating from the dressing.

In the embodiment illustrated a polyester fibre sheet 3 consisting of directional fibres is attached to the other side of the woven fabric sheet 2. This polyester fibre sheet 3 is also attached by needle punching and is 1.7 mm thick. In this embodiment the surface 11 of the sheet 3 is not heat-treated and thus has no glazed finish.

Strike through, whereby exudates come through the dressing, is prevented or diminished by the glazed layer, in conjunction with the polycotton support surface. This combination also acts to encourage the rapid wicking of fluid between the glazed and absorbent support surface by capillary action towards the outside edge of the dressing fabric. This wicking effect is further enhanced by the glazed surface not adhering to the wound or becoming saturated.

The dressing illustrated may be used in conjunction with a similar dressing to form a composite dressing. The two unglazed surfaces are placed together, such that fluids absorbed into the dressing that contacts the wound bed pass from this dressing via the polyester fibres to the second dressing. This substantially increases the quantity of fluid that the dressing can absorb.

In further embodiments, not shown, the polyester fibre sheet 3 may be omitted. Omitting this sheet gives a thinner dressing, which can therefore be more easily manipulated. It has been found that this sort of dressing is particularly well adapted for veterinary and in particular, equestrian use. The bandaging of horse's legs requires a dressing that is very flexible and can bend to the shape of the leg.

In other embodiments, not shown, the second outer surface 11 may also be heat-treated. The advantage of this is that it facilitates the removal of adhesive tapes that bind the dressing to the patient or to other dressings, and thus limits any disturbance caused to the dressing.

In other embodiments, neither side of the surgical dressing is heat glazed. In these embodiments the absorbent fabric comprises a mixed yarn of between 60 to 70% polyester and 40 to 30% cotton, most preferably 65% polyester and 35% cotton. Other properties of the dressing are the same as for the embodiments described above.

The dressing may also be used as a surgical drain. The draining action of the fabric is achieved by cutting the dressing to size depending upon the depth of the wound bed. A typical draining strip is 10 mm in width. The length is dependent on the distance over which the exudate or fluid needs to be transported. One end of the drain is held in the wound and the other end drain is received in a collection device or bag. The drain attaches to a dressing or absorbent device by weaving in and out of slots cut in the dressing or device. The fabric has the advantage of wicking fluid vertically whilst the outer surfaces of the fabric remain comparatively dry.

In some embodiments the drain may have both surfaces heat glazed. Heat glazing both sides enables adhesive tape that may be used to secure, for example, a stoma bag to the patient's wound to be removed easily. This means that the bag can be changed without disturbing the drain.

This method of removing exudate or other fluids from a cavity wound or sinus provides for healing within the wound bed. The fabric structure of the dressing is such that it allows for the original tensile strength to be maintained whilst saturated.

The drain may also be used to divert exudate from a sinus away from an existing wound face, thereby reducing the risk of reinfection from the sinus channel. This is achieved by inserting the dressing cut to form a drain and with a tapered end directly into the cavity or sinus channel, and bending the drain in the direction of a collection bag.

The dressing according to embodiments of the invention may be used for a variety of wounds including chronically infected wounds, exudating wounds, venous ulcers, pressure ulcers, burns, tears, both in humans and animals. They are particularly appropriate for venous ulcers as they can be bound tightly to produce a degree of compression without sticking to the wound. They may also be used to hold hydrogels, used to rehydrate wounds, in place. It has been found that the glazed surface of the dressing has a low absorption of the dense hydrogel, while absorbing the exudates well.

The invention claimed is:

1. A dressing for transporting exudates and other fluids away from a wound, the dressing comprising:
   a first layer comprising a plurality of synthetic fibres;
   a woven absorbent fabric layer; and
   a second layer comprising a plurality of synthetic fibres, wherein each of said first and second layers having an inner surface in contact with said woven layer and an outer surface; said outer surfaces are heat treated to hinder individual fibres from extending out of that part of the outer surface, giving a glazed effect to that part of the outer surface wherein, each of said first and second layers is attached to said woven layer by needle punching from the respective outer surfaces, said needle punching forming a plurality of directional fibres arranged to provide a wicking path along the directional fibres from the outer surfaces of the first and second layers to a surface of the absorbent fabric, such that fluids contacting the outer surface are wicked away from the outer surface along the synthetic fibres towards the absorbent fabric.

2. A dressing according to claim 1, wherein the absorbent fabric comprises a woven polycotton fabric.

3. A dressing according to claim 2, wherein the absorbent fabric is scoured after weaving.

4. A dressing according to claim 1, wherein the absorbent fabric comprises a mixed yarn of between 60% to 70% polyester and 40% to 30% cotton.

5. A dressing according to claim 1, wherein the absorbent fabric comprises a mixed yarn of substantially 65% polyester and 35% cotton.

6. A dressing according to claim 2, wherein the absorbent fabric is woven from threads having an average diameter of 68 nm.

7. A dressing according to claim 1, wherein the synthetic fibres are polyester fibres.

8. A dressing according to claim 1, wherein the whole of the outer surface is heat-treated.

9. A dressing according to claim 1, wherein the dressing is substantially planar and has a density of between 710 and 735 g/m$^2$.

10. A dressing comprising two dressings according to claim 1, the dressings being arranged adjacent to each other such that respective outer surfaces of the two dressings contact each other.

11. A dressing according to claim 10, the two dressings being arranged such that the second outer surfaces of the two dressings contact each other.

12. A dressing according to claim 1, wherein the thickness of the dressing is between 1 and 4 mm.

13. A dressing according to claim 12, wherein the thickness of the dressing is between 3 and 3.5 mm.

14. A dressing according to claim 1, wherein the dressing is arranged to act as a drain.

15. A dressing according to claim 14, wherein the absorbent fabric and synthetic fibres form a strip substantially 10 mm wide.

16. A method of manufacturing a dressing, the method comprising the steps of;
   attaching a first layer comprising a plurality of synthetic fibres to one surface of an absorbent woven central support fabric by needling;
   attaching a second layer comprising a plurality of synthetic fibres to another surface of said absorbent woven central support fabric by needling, each of said first and second layers having an inner surface in contact with said support fabric and an outer surface, said needling is done such that at least some of the synthetic fibres in said first and second layers are arranged directionally to form a wicking path between each outer surface and the absorbent support fabric; and heating at least a part of the outer surface of said first and second layers to impede individual fibres from extending out of that part of the surface, giving a glazed effect to that part of the surface.

17. A method of manufacturing a dressing according to claim 16, the heating step comprising heating the at least a part of the outer surface to a temperature between 200 and 250° C.

18. A manufacturing method according to claim 16, the heating step comprising passing heated rollers over the at least a part of the outer surface to heat that part of the outer surface.

19. A manufacturing method according to claim 16, the heating step comprising heat-treating the at least a part of the outer surface by singeing it with a flame.

20. A manufacturing method according to claim 16, the attaching step comprising pushing the synthetic fibres through the support surface using needle punching to attach them to the absorbent support fabric.

* * * * *

UNITED STATES PATENT AND TRADEMARK OFFICE
CERTIFICATE OF CORRECTION

| | | |
|---|---|---|
| PATENT NO. | : 7,112,712 B1 | Page 1 of 1 |
| APPLICATION NO. | : 10/129624 | |
| DATED | : September 26, 2006 | |
| INVENTOR(S) | : Ancell | |

It is certified that error appears in the above-identified patent and that said Letters Patent is hereby corrected as shown below:

Title page, under Item (22) PCT Filed: "Nov. 10, 1999" should read --Nov. 9, 2000--

Signed and Sealed this

Nineteenth Day of December, 2006

JON W. DUDAS
*Director of the United States Patent and Trademark Office*